US008983026B2

(12) United States Patent
Ishiyama (10) Patent No.: US 8,983,026 B2
(45) Date of Patent: Mar. 17, 2015

(54) X-RAY CT SYSTEM

(75) Inventor: Fumio Ishiyama, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 402 days.

(21) Appl. No.: 13/415,309

(22) Filed: Mar. 8, 2012

(65) Prior Publication Data

US 2012/0230466 A1    Sep. 13, 2012

(30) Foreign Application Priority Data

Mar. 10, 2011    (JP) ................................. 2011-052332

(51) Int. Cl.
| H05G 1/32 | (2006.01) |
| A61B 6/03 | (2006.01) |
| A61B 6/00 | (2006.01) |
| H05G 1/58 | (2006.01) |

(52) U.S. Cl.
CPC ................. *A61B 6/035* (2013.01); *A61B 6/405* (2013.01); *A61B 6/4435* (2013.01); *A61B 6/482* (2013.01); *H05G 1/58* (2013.01); *A61B 6/503* (2013.01)
USPC ............................................ 378/16; 378/105

(58) Field of Classification Search
USPC ........................................ 378/105, 106, 4–20
See application file for complete search history.

(56) References Cited

U.S. PATENT DOCUMENTS 5,400,385 A * 3/1995 Blake et al. .................... 378/110

FOREIGN PATENT DOCUMENTS

| CN | 1923138 A | 3/2007 |
| CN | 101203085 A | 6/2008 |
| CN | 101529995 A | 9/2009 |
| JP | 60-163400 | 8/1985 |
| JP | 62-047998 | 3/1987 |
| JP | 2556903 | 8/1997 |
| JP | 2011-005183 | 1/2011 |
| JP | 2011-104066 | 6/2011 |
| WO | WO 2007/000971 A1 | 1/2007 |
| WO | WO 2009/147574 A1 | 12/2009 |

OTHER PUBLICATIONS

Combined Chinese Office Action and Search Report issued Jun. 26, 2014 in Patent Application No. 201210061644.2 (with English Translation of Category of Cited Documents).
Office Action issued Dec. 2, 2014 in Japanese Patent Application No. 2011-052332.

* cited by examiner

*Primary Examiner* — Hoon Song
(74) *Attorney, Agent, or Firm* — Oblon, McClelland, Maier & Neustadt, L.L.P.

(57) ABSTRACT

An X-ray tube and an X-ray detector are arranged opposing one another. X-rays are irradiated from the X-ray tube by revolving around the subject. An X-ray image is obtained based on the X-rays that penetrate the subject and are detected by the X-ray detector. The high voltage generator has an inverter that supplies a voltage to the X-ray tube by switching to a predetermined operating frequency during revolution of the X-ray tube. Regarding the frequency adjustable part, the operating frequency of the inverter is adjustable such that it is a multiple of the collection rate, which is the number of X-ray images obtained per one revolution of the X-ray tube. The timing generator may adjust the voltage supplied to the X-ray tube at a timing synchronized with the operating frequency of the inverter.

6 Claims, 14 Drawing Sheets

TABLE A

| COLLECTING RATE R | MULTIPLYING FACTOR |
|---|---|
| 600 | 2 |
| 900 | 3 |
| 1200 | 4 |

FIG. 6

TABLE B

| ROTATION CYCLE [sec] | MULTIPLYING FACTOR |
|---|---|
| 0.35 | 19 |
| 0.5 | 28 |
| 1.0 | 56 |

X-RAY CT SYSTEM

CROSS-REFERENCE TO RELATED APPLICATION

This application is based upon and claims the benefit of priority from Japanese Patent Application No. 2011-052332, filed Mar. 10, 2011; the entire contents of which are incorporated herein by reference.

FIELD

Embodiments of the present invention relate to an X-ray CT system.

BACKGROUND

Conventionally, as a technique for conducting analysis on substances, for example, there is a dual energy CT that applies two different types of tube voltages to an X-ray tube and conducts imaging with X-rays irradiated from the X-ray tube. When a substance is imaged by X-rays at an altered tube voltage, the substance exhibits a peculiar change in CT value. Based on this change in CT value, for example, contrast agents for blood vessels and calcified tissues may be analyzed.

An example of a dual energy CT is conducting imaging by means of two X-ray tubes by simultaneously irradiating one subject with X-ray from one X-ray tube with a high voltage applied and another X-ray tube with a low voltage applied.

Another example of a dual energy CT is imaging by using one X-ray tube to change the tube voltage while revolving X-ray tube, irradiating the subject alternately with X-rays of two types of tube voltages, high voltage and low voltage. Furthermore, the X-ray tube and an X-ray detector are arranged opposing one other and fixed to a revolving ring, with the revolving ring supported by a frame. In the following description, the revolution of the X-ray tube refers to an overall revolution of the revolving ring and the X-ray detector provided to the revolving ring, etc.

The X-ray generator, which generates X-rays by applying a tube voltage to the X-ray tube, is an inverter type to be smaller and lighter in weight. Regarding the X-ray generator with a tube voltage generator of an inverter type, the operating frequency component of the inverter inevitably tends to remain at the tube voltage. In such cases, the X-ray dosage emitted by the X-ray tube is also affected by the operating frequency component. Therefore, when altering the tube voltage during revolution of the X-ray tube, the above analysis is restricted by the timing of switching the tube voltage between high voltage and low voltage (tube voltage switching frequency) and the operating frequency of the inverter.

When the inverter operating frequency is sufficiently higher than the tube voltage switching frequency (for instance, 100 times or more), the inverter may be operated independently from the timing for switching the tube voltage. However, for example, if the tube voltage switching frequency is increased for cardiac diagnosis and the tube voltage switching frequency approaches the inverter operating frequency, there is a problem of declined reproducibility of the tube voltage waveform repeating the waveform at the same amplitude in any cycle. That is to say, there is a problem of the variation width of the tube voltage being different at every tube voltage switching cycle.

Next, this problem is described in detail.

The tube voltage switching frequency fs [Hz] may be expressed by the following formula.

$$fs = R/(T*2) \quad (1)$$

Here, R is the collection rate, which is the number of X-ray images obtained per one revolution of the X-ray tube [view/rot], and T is the revolution time per one revolution of the X-ray tube [sec/rot].

For example in cardiac diagnosis, when R=900, T=0.35, the tube voltage switching frequency fs is 1285.71 [Hz] from the formula (1). Further, the tube voltage switching cycle Ts is 777.78 [μS].

Moreover, when the inverter repeats increase and decrease of the tube voltage, the clock number Nc required for a cycle period may be expressed by the following formula.

$$Nc = Ts/Ti \quad (2)$$

Here, Ti is the operating cycle of the inverter [sec].

For example, in cardiac diagnosis, when the fundamental frequency fr of the inverter is 25 [kHz], the operating cycle of the inverter Ti is 40 [μs]. The clock number Nc calculated from the formula above (2) becomes 19.44.

However, since the inverter only operates in clock units in fact, the clock number Nc required for the cycle period may be 19 or 20. This dispersion of the clock number causes declined reproducibility of waveforms of the tube voltage.

Figure 16:
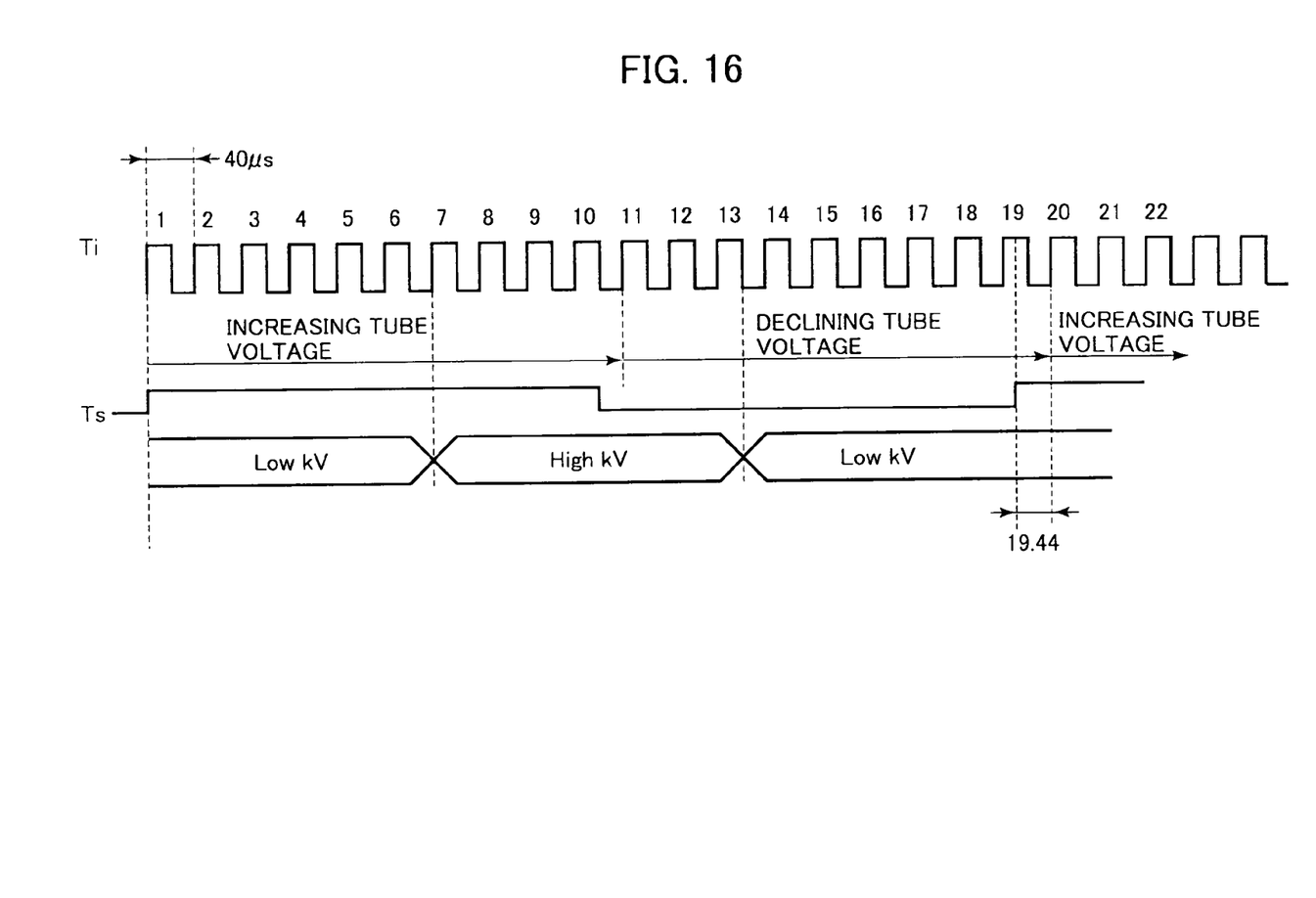
FIG. 16 is a time chart of the operating cycle (cycle of the clock) of the inverter and the timing for switching the tube voltage.

FIG. 16 is a timing chart of an operating cycle (cycle of the clock) of the inverter and the timing for switching the tube voltage. As illustrated in FIG. 16, in the example mentioned above, when the tube voltage switching cycle Ts is 777.78 [μS] and the operating cycle Ti of the inverter is 40 [μS], the clock number Nc becomes 19.44.

Figure 17:
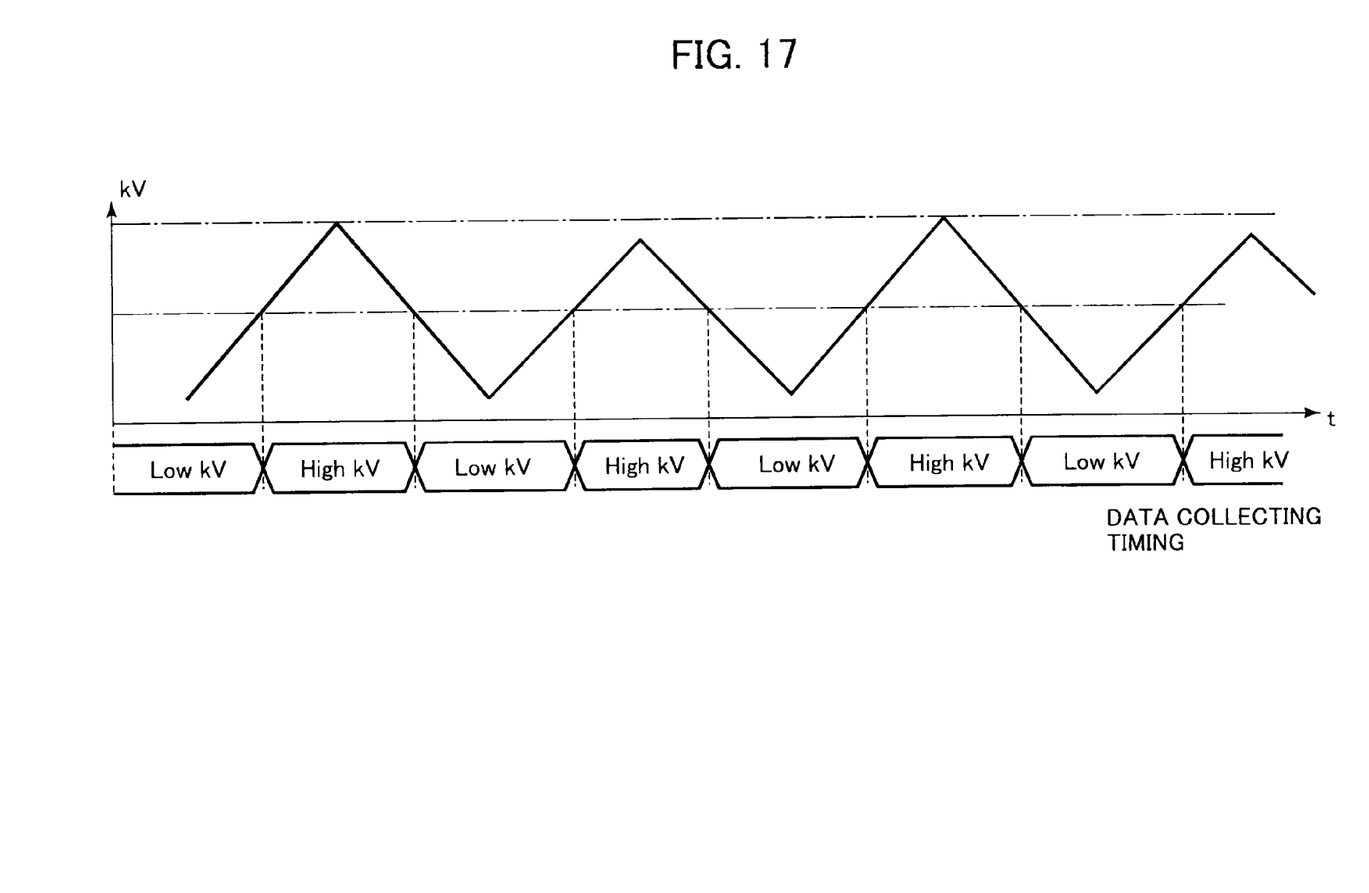
FIG. 17 is a diagram illustrating the tube voltage waveform.

FIG. 17 is a diagram illustrating the tube voltage waveforms. As illustrated in FIG. 17, the clock number Nc required for the cycle period may be 19 or 20 when the inverter repeats increase and decrease of the tube voltage. Therefore, the waveform of the tube voltage is dispersed.

As described above, when the tube voltage switching frequency is high upon cardiac diagnosis, etc., and is close to the inverter operating frequency, there is a problem of the reproducibility of the tube voltage waveform declining.

Moreover, a balancer is provided to the revolving ring provided with the X-ray tube, the X-ray detector and the X-ray generator, etc. Nevertheless, fluctuation appears while revolving. This fluctuation disadvantageously causes loss of X-ray images of high quality.

This embodiment is intended to provide an X-ray CT system that generates a tube voltage waveform with good reproducibility upon dual energy CT, so as to obtain high-quality X-images.

DETAILED DESCRIPTION

[First Embodiment]

Figure 1:
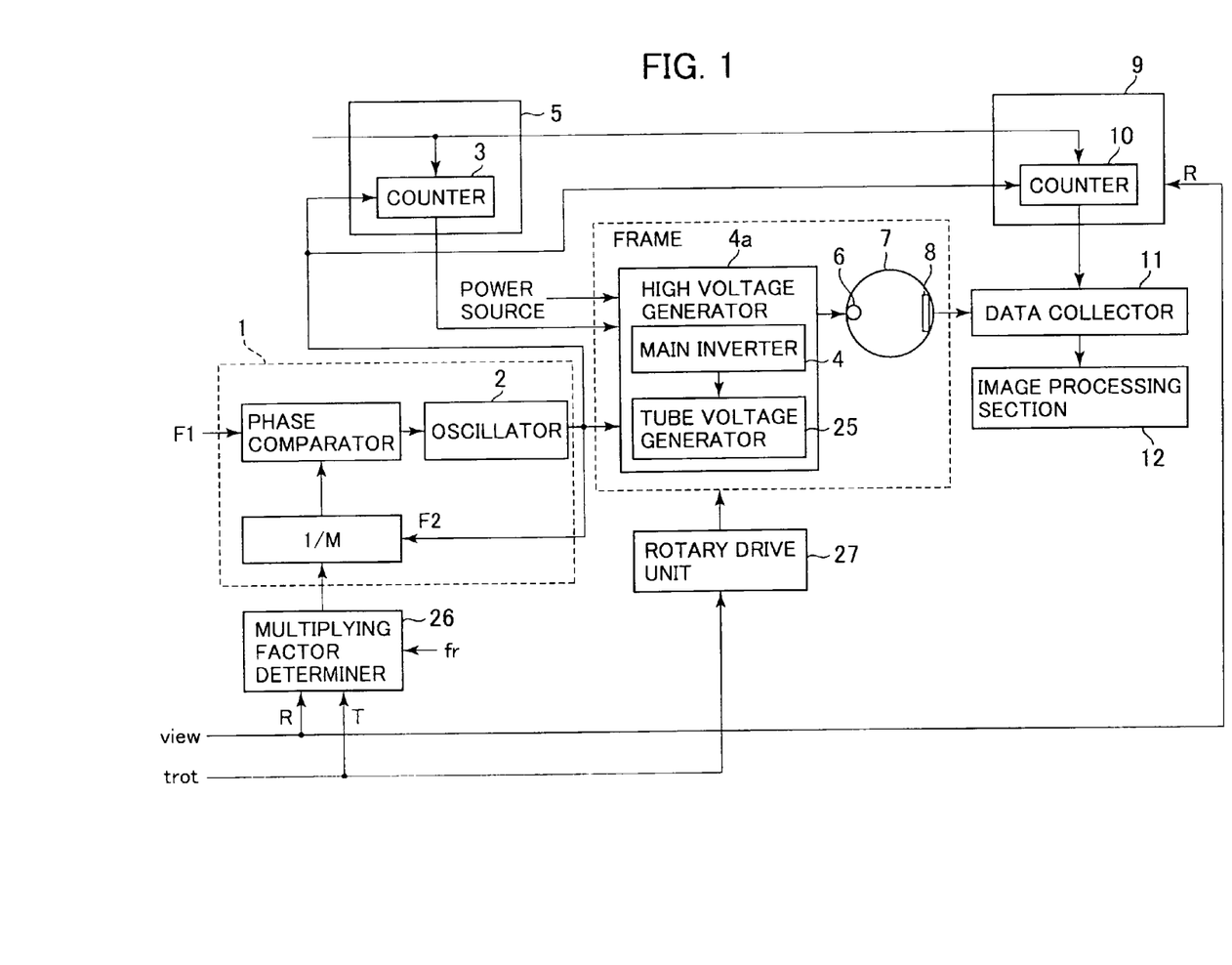
FIG. 1 is a block diagram illustrating the configuration of the X-ray CT system pertaining to the first embodiment.

The first embodiment of the X-ray CT system is described with reference to FIG. 1. FIG. 1 is a block diagram illustrating the configuration of the X-ray CT system.

The X-ray CT system comprises a multiplier 1 to synchronize the inverter operating frequency fi with the tube voltage switching frequency fs, a high voltage generator 4a with a main inverter 4 and a tube voltage generator 25, and a counter 3, in addition to comprising an up-down timing generator 5 that outputs instructions to a main inverter 4 to switch the tube voltage, a revolving ring 7 in which an X-ray tube 6 and an X-ray detector 8 are arranged opposing one another, a data collector 11 that collects the X-rays detected by the X-ray detector 8 at a predetermined collection timing, and a counter 10, and further comprising a collection timing generator 9 that outputs instructions for collecting timing to the data collector 11, an image processing section 12 that reconstructs the X-ray image based on the X-ray collected by the data collector 11, a rotary drive unit 27 that revolves the revolving ring 7 based on a revolution cycle T per one revolution of the X-ray tube 6 (revolving ring 7), and a multiplying factor determiner 26 that determines the multiplying factor based on collection rates R when the X-ray images are collected per one revolution of the revolution cycle T and the X-ray tube 6 and output to the multiplier 1.

The multiplier 1 is set forth by an example of PLL (Phase Locked Loop). Moreover, the multiplier 1 is generalized by a "frequency converting circuit." Here, "synchronize" refers to specifically having the inverter operating frequency fi be a multiple of the tube voltage switching frequency fs.

Next, an example of PLL is set forth. The multiplier 1 comprises a phase comparator that compares the phase difference between two signals to generate a difference signal, a loop filter that cuts an alternating-current component, and an oscillator (OSC). The phase comparator compares phases between the target signals (frequency Fl) input from the outside and the comparison signals generated from a re-running oscillator (frequency F2) of the oscillator, outputting the phase difference signal to the loop filter. The loop filter generates the control voltage based on the phase difference signal, which is output to the oscillator. The oscillator outputs the target signal and the output signal synchronized to the phase thereof to the outside based on the input control voltage. Moreover, as a result, the multiplier 1 synchronizes the frequency of the output signal with the target signal.

FIG. 1 illustrates the multiplier 1 with a phase comparator, the oscillator 2, and a frequency divider. The frequency divider divides the output signal of the oscillator 2 to 1/M. The phase comparator compares the frequency F1 of the target signal with the frequency of the divided signal (F2/M), to output the phase difference signal to the loop filter (not illustrated). By means of the control voltage due to the loop filter, the oscillator 2 oscillates the signal of the frequency synchronizing with the target signal. Thereby, the multiplier 1 outputs the output signal of the frequency synchronizing with the frequency F1 of the target signal.

Next, the operation of the multiplier 1 is described with reference to FIG. 1. The fundamental frequency fr [kHz], revolution cycle T [sec], which is the revolution time per one revolution of the X-ray tube, and the collection rate R [view/rot], which is the number of X-ray images acquired per one revolution of the X-ray tube, are input to the multiplying factor determiner 26. Furthermore, the fundamental frequency fr is the frequency of the comparison signal generated by the abovementioned oscillator of the multiplier 1.

The multiplying factor determiner 26 determines the clock number Nc=19.44 required for the cycle period of the inverter repeating increase and decrease of the tube voltage based on the input fr, T, and R using the following formula.

$$Nc=(fr*T*2)/R \qquad (3)$$

Here, fr=25, T=0.35, and R=900.

The multiplying factor determiner 26 rounds down the Nc=19.44 after the decimal point to determine Nc=19. By rounding down after the decimal point, the inverter operating frequency fi is 19 times more (a multiple) than the tube voltage switching frequency fs. As mentioned above, the reason for rounding down after the decimal point is that reproducibility of the tube voltage waveform declines if the inverter operating frequency fi is not made a multiple of the tube voltage switching frequency fs.

The 1/M of the multiplier 1 is determined from the obtained Nc=19. The multiplier 1 multiplies the frequency F2 of the oscillator by 1/M and compares it with the frequency F1 of the target signal. The frequency F2 of the oscillator is synchronized with the frequency F1 of the target signal.

Moreover, the synchronized frequency F2 of the oscillator, that is to say, the inverter operating frequency fi=24.43 [kHz], may be determined by the following formula. Note that Nc=19.

$$fi=Nc*R/(T*2) \qquad (4)$$

The multiplier 1 outputs a pulse of the inverter operating frequency fi=24.43 [kHz] to the counter 3 and the main inverter 4. Note that, the up-down timing generator 5 outputs the instruction to commence counting to the counter 3, and in addition, outputs an increasing actuating signal to increase the tube voltage to the main inverter 4, and following commencement of counting, outputs the tube voltage switching actuating signal to switch the decrease and increase of the tube voltage to the main inverter 4 based on the count rate (number of pulses) from the counter 3.

Figure 3:
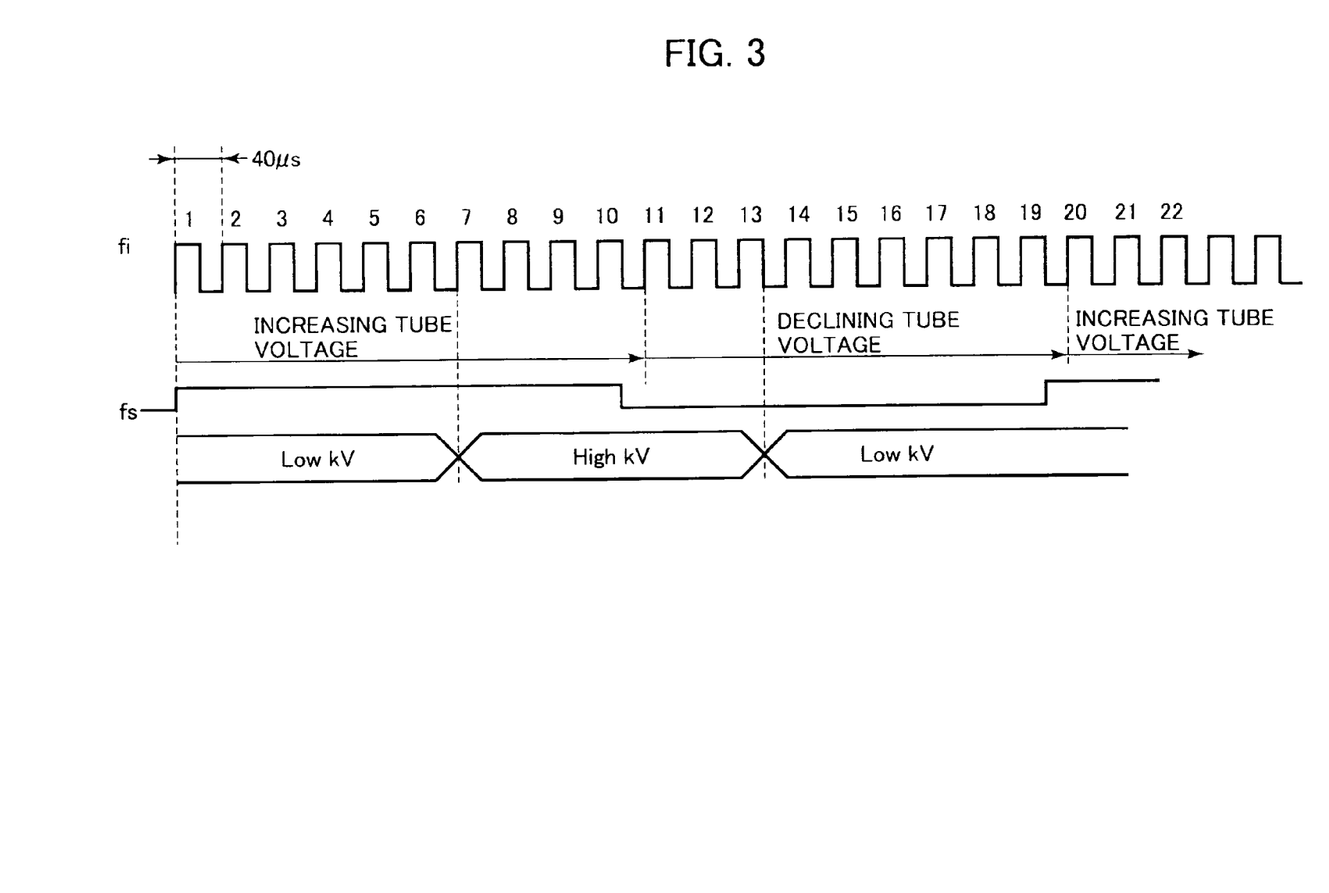
FIG. 3 is an explanatory drawing of the operation of the inverter, as well as a time chart of the operating cycle (cycle of the clock) of the inverter, and timing for switching the tube voltage.

Next, the operation of the main inverter 4 is described with reference to FIG. 3 and FIG. 4. FIG. 3 is an explanatory drawing of the operation of the inverter, the operating cycle (cycle of the clock) of the inverter, and the time chart of the timing for switching tube voltage. As illustrated in FIG. 3, for example, in response to the increasing actuating signal from the up-down timing generator 5: the main inverter 4 is turned on; the increasing operation of the tube voltage is conducted; the count value "9" is received from the counter 3; the up-down timing generator 5 outputs the tube voltage switching actuating signal to the main inverter 4; the main inverter 4 turns off; the decreasing operation of the tube voltage is conducted; the count value "19" is received from the counter 3; the up-down timing generator 5 outputs the tube voltage switching actuating signal to the main inverter 4; and the main inverter 4 conducts the increasing operation of the tube voltage.

That is to say, the up-down timing generator 5 has no dispersion per clock number Nc=19, and outputs the instruction to switch the tube voltage to the main inverter 4. Thereby, the inverter operating frequency fi becomes 19 times more (a multiple) than the tube voltage switching frequency fs, allowing the inverter operating frequency fi to be synchronized to the tube voltage switching frequency fs. Note that the up-down timing generator 5 is generalized by "timing generator."

By having the inverter operating frequency fi 19 times more (a multiple) than the tube voltage switching frequency fs, the reproducibility of the tube voltage waveform may be improved upon dual energy CT.

In response to the tube voltage waveform with good reproducibility, the X-ray tube 6 alternately irradiates X-rays at the prescribed high voltage and X-rays at the prescribed low voltage to the subject. Among clocks 1 to 19, the tube voltage generator 25 supplies the tube voltage between the clocks 7 to 13 (high voltage: Hight kV) to a high voltage power supply 64 (Refer to FIG. 7) and the X-ray tube 6 irradiates X-rays under high pressure. Furthermore, among the clocks 1 to 19, the tube voltage generator 25 supplies the tube voltage between the clocks 14 to 19 and 1 to 6 (low voltage: Low kV) to the voltage power supply 64 and the X-ray tube 6 irradiates X-rays under low voltage.

The collection timing generator 9 outputs instructions for collecting data to the data collector 11 based on the collection rate R and the clock number counted by the counter 10.

Figure 4:
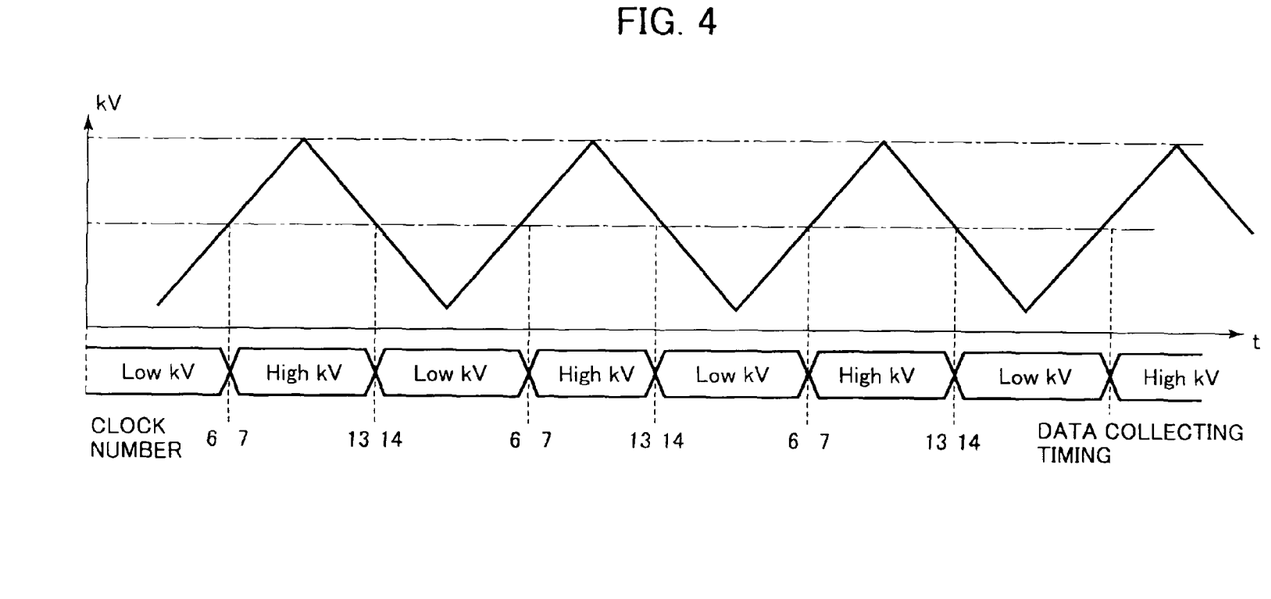
FIG. 4 is a diagram illustrating the tube voltage waveform.

FIG. 4 is a diagram illustrating the tube voltage waveform. As illustrated in FIG. 4, among the clocks 1 to 19, the X-rays irradiated under high voltage of clocks 7 to 13 are collected, and among the clocks 1 to 19, the X-rays irradiated under low voltage of clocks 14 to 6 are collected. Thereby, the data collector 11 may collect the X-rays irradiated under high voltage and low voltage with no time lag, and the image processing section 12 may acquire high-quality X-ray images based on the collected data. Furthermore, the collection timing generator 9 and the data collector 11 are generalized by "image data acquisition part."

[Second Embodiment]

The first embodiment set forth an X-ray CT system that synchronizes the inverter operating frequency fi to the tube voltage switching frequency fs to acquire high-quality X-ray images.

Figure 2:
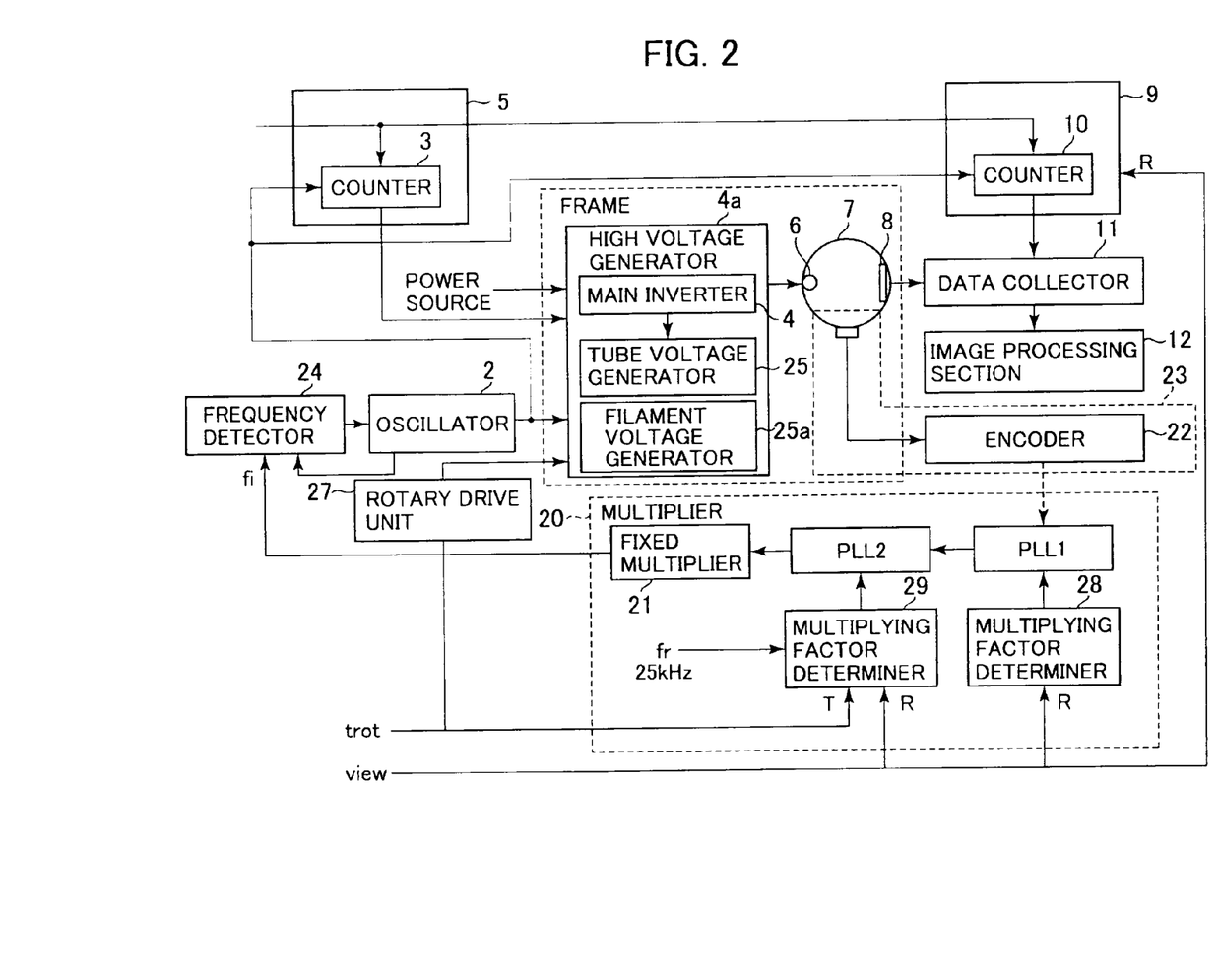
FIG. 2 is a block diagram illustrating the configuration of the X-ray CT system pertaining to the second embodiment.

With reference to FIG. 2, the X-ray CT system pertaining to the second embodiment in order to acquire further high-quality X-ray images will be described that comprises a multiplier 20 to synchronize the inverter operating frequency fi with the fluctuations occurring during revolution of the X-ray tube 6. Note that regarding those items of the same configuration as the X-ray CT system of the first embodiment, the same number is attached and explanations thereof are omitted.

FIG. 2 is a block diagram illustrating the composition of the X-ray CT system. As illustrated in FIG. 2, the multiplier 20 comprises adjustable multipliers PLL1, PLL2, and a fixed multiplier 21. Moreover, an encoder 22 and a frequency detector 24 are also provided. Here, the fundamental performance of the adjustable multipliers PLL1, PLL2 are the same as the multiplier 1 mentioned above, so explanations thereof are omitted. Furthermore, the multiplier 20 is generalized by "frequency converting circuit." In addition, the pulse signal detection circuit 23 is generalized by "frequency detector."

Figure 5:
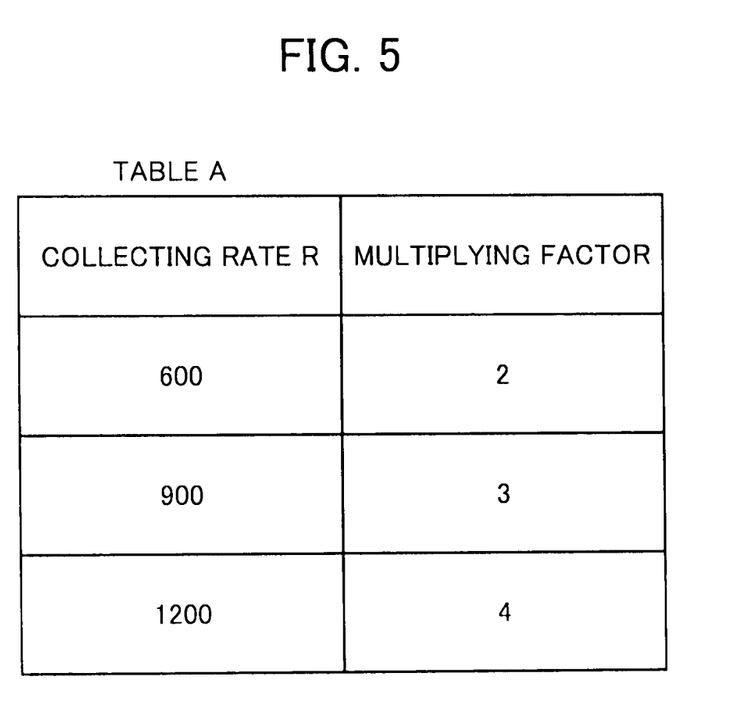
FIG. 5 is a diagram of a table that was recorded associating the collection rate with the multiplying factor.

Next, the operation of the X-ray CT system is described with reference to FIGS. 2 to 6. FIG. 5 is a diagram of recorded Table A by associating the collection rate with the multiplying factor.

The encoder 22 is integrally provided with a revolving ring 7 and comprises a disc with through holes made in the circumference at equal intervals as well as a pulse signal detection circuit 23 that outputs pulse signals by receiving the detection light passing through the through holes.

When the rotary drive unit 27 revolves the revolving ring 7 and the X-ray tube 6 is revolving at a predetermined speed of revolution by receiving instructions via operations from an operating part (not illustrated) (revolution frequency per one revolution), the disc integrally revolves with the revolving ring 7 and the pulse signal detection circuit 23 outputs one pulse signal (300 pulse signals at a revolution of 360 degrees) to the adjustable multiplier PLL1 each time the X-ray tube 6 revolves 1.2 degrees, for example. The multiplying factor determiner 28 comprises Table A illustrated in FIG. 5. Based on the number of pulses Np per one rotation of the X-ray tube 6 as well as the collection rate R per one rotation of the X-ray tube 6, the multiplying factor is obtained with reference to Table A. The adjustable multiplier PLL1 multiplies the detection signal by the determined multiplying factor, and transmits this to the PLL2.

For example, when Np=300 and R=900, the multiplying factor determiner 28 reads out the multiplying factor 3 with reference to Table A, and the adjustable multiplier PLL1 outputs the signal that multiplied (3 times) the detection signal to the PLL2.

Next, the multiplying factor determiner 29 obtains the tube voltage switching frequency fs [Hz] by applying the revolution cycle T [sec] and the collection rate R of the X-ray tube 6 to formula (1).

$$fs=R/(T*2) \quad (1)$$

For example, when T=0.5 and R=900, the multiplying factor determiner 29 obtains the tube voltage switching frequency fs=900 by using formula (1).

Moreover, the multiplying factor determiner 29 uses the following formula to obtain the multiplying factor $\mu$.

$$\mu=INT(fr/(fs+0.5)) \quad (5)$$

By means of INT, which is a symbol to round down the obtained numerical value after the decimal point, the multiplying factor $\mu$ becomes an integer.

Figure 6:
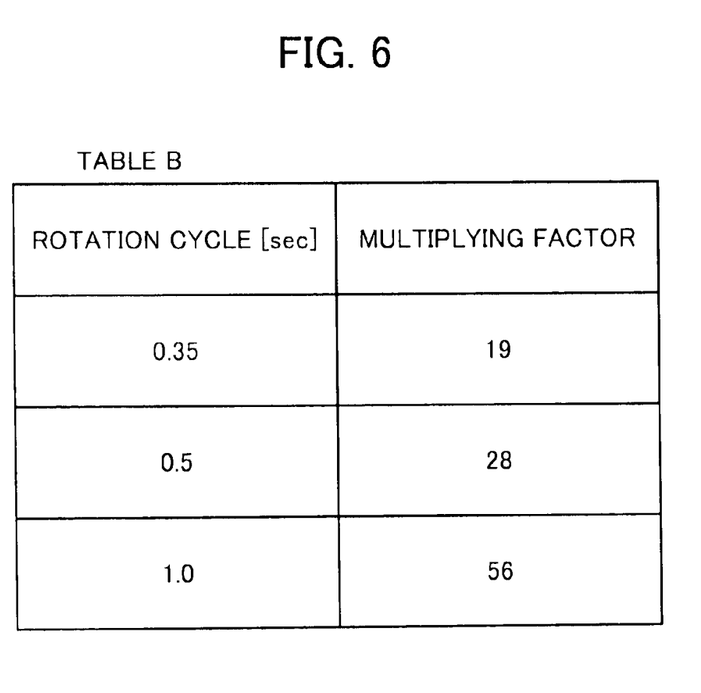
FIG. 6 is a diagram of a table that was recorded associating the revolution frequency with the multiplying factor of the X-ray tube.

FIG. 6 is a diagram illustrating records Table B that associates the revolution cycle T of the X-ray tube with the multiplying factor. As illustrated in FIG. 6, when the tube voltage switching frequency fs=900, the correspondence of the revolution cycle T of the X-ray tube 6 with the multiplying factor becomes: the multiplying factor $\mu$=19 when T=0.35 [sec]; the multiplying factor $\mu$=28 when T=0.5 [sec]; and the multiplying factor $\mu$=56 when T=1 [sec].

In this embodiment, the multiplying factor determiner 29 comprises Table B. When fs=900 and fr=25 [kHz], $\mu$=28 is obtained with reference to Table B.

The adjustable multiplier PLL2 outputs the multiplied (28 times more) signal from the PLL1 to the frequency detector 24. The frequency of signals input to the frequency detector 24 becomes the inverter operating frequency fi [kHz]. When $\mu$=28 and fs=900, fi=25.2.

When the main inverter 4 is a line commutation type and a bridge type, the fixed multiplier 21 outputs signals with twice the frequency of the inverter operating frequency fi 2 (50.4 [kHz]) to the frequency detector 24.

The frequency detector 24 compares the oscillatory frequency fo of the oscillator 2 with the frequency that is double the inverter operating frequency fi which is output from the fixed multiplier 21, and controls such that the oscillatory frequency fo has double the frequency of the inverter operating frequency fi. The oscillator 2 outputs pulses that are double the frequency of the inverter operating frequency fi.

As described, the inverter operating frequency fi of the main inverter 4 is synchronized with the fluctuation occurring during the revolution of the X-ray tube 6, thereby, allowing further high-quality X-ray images to be obtained.

Note that the multiplying factor of respective Tables A and B is determined by the following. Generally, when outputting a direct voltage produced by an appropriately operating inverter, the frequency of the inverter will be mostly determined. Thus, in the case of this embodiment, the fundamental frequency fr thereof is determined as 25 [kHz]. Therefore, the inverter operating frequency fi is made adjustable in order to synchronize. However, this is limited to frequencies near the 25 [kHz]. In other words, the multiplying factor of respective Tables A and B is made a multiplying factor that becomes a frequency that may be synchronized near 25 [kHz].

Note that the frequency detector 24 and the oscillator 2 may be removed, yielding a configuration in which the output of the multiplier 20 is directly input to the high voltage generator 4a.

Moreover, the system has a configuration that absorbs revolution irregularities in the description above. However, if synchronization alone is necessary without absorbing the revolution irregularities, the pulse corresponding to the number of pulses (for example, 300 pulses/rot) that changes according to the speed of revolution may be entered instead of the output from the pulse signal detection circuit 23.

[Third Embodiment]

Next, the X-ray CT system pertaining to the third embodiment is described with reference to FIGS. 7 to 15.

Figure 7:
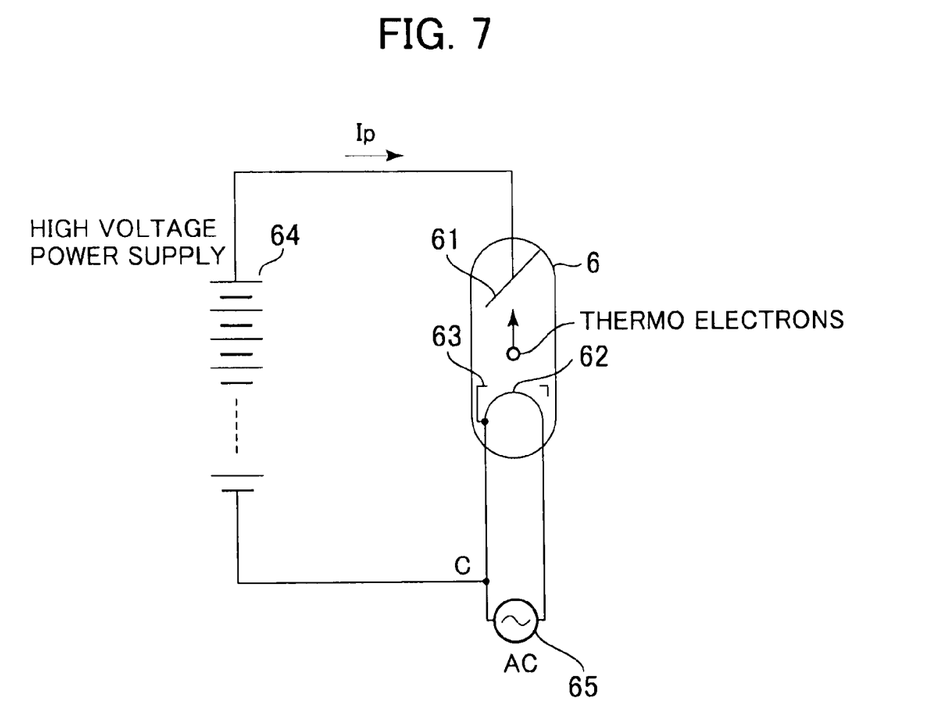
FIG. 7 is a circuit diagram of the X-ray generator.

FIG. 7 is a circuit diagram of the X-ray CT system. As illustrated in FIG. 7, an anode 61 of the X-ray tube 6 is connected to the plus terminal of a high voltage power supply 64, while a cathode 62 is connected to the minus terminal of a high voltage power supply 64. A filament power supply 65 is provided to yield thermo electrons from the cathode 62.

Figure 8:
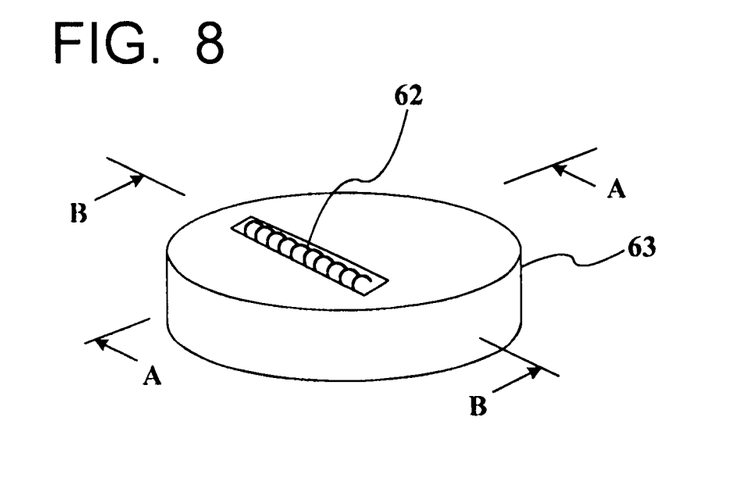
FIG. 8 is a perspective diagram of the cup.
Figure 9:
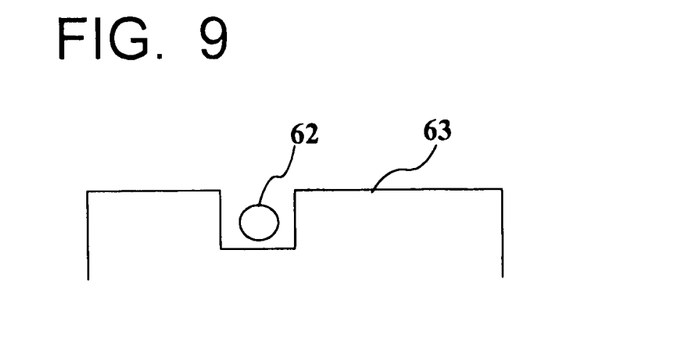
FIG. 9 is an A-A wire cross-section of FIG. 8.
Figure 10:
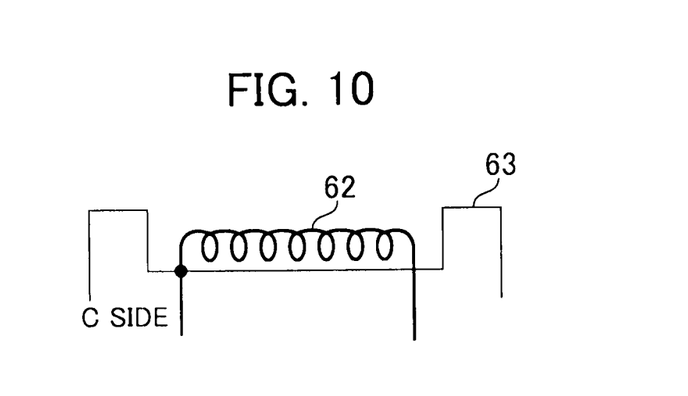
FIG. 10 is a B-B wire cross-section of FIG. 8.

FIG. 8 is a perspective diagram of the cup. FIG. 9 is a A-A wire cross-section of FIG. 8. FIG. 10 is a B-B wire cross-section of FIG. 8. As illustrated in FIGS. 8 to 10, the cathode 62 is provided in the groove of a cup 63. One contact point of the cathode 62 is connected to the cup 63, while another contact point has potential towards the cup 63. Furthermore, the cathode 62 may be referred to as a filament.

When the cathode 62 of the X-ray tube 6 is turned on by the alternating current of the filament power supply 65, an abnormality occurs in the emission of the thermo electrons due to the potential difference of the cathode 62 of the X-ray tube 6 and the cup 63, changing the X-ray output.

Figure 11:
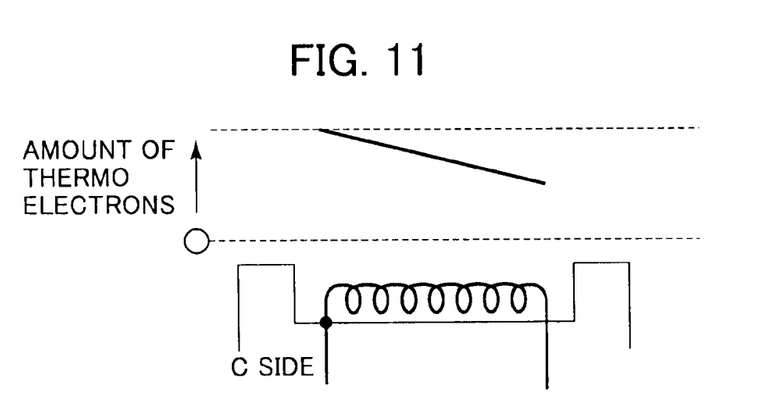
FIG. 11 is a diagram indicating the amount of thermo electrons when the end of the filament has a positive potential towards the cup.
Figure 12:
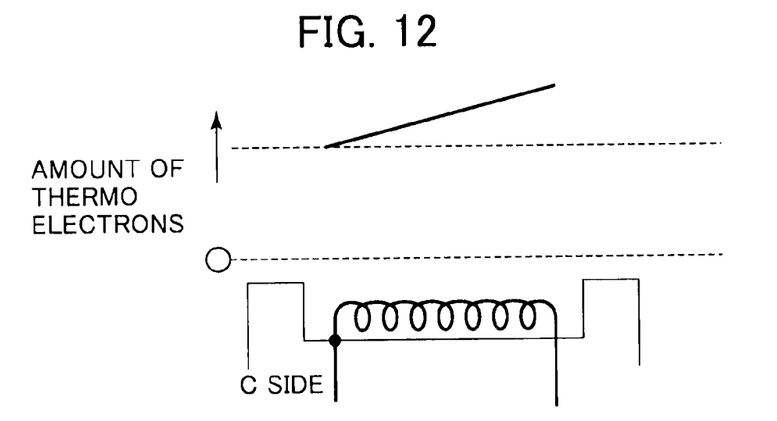
FIG. 12 is a diagram indicating the amount of thermo electrons when the end of the filament has a negative potential towards the cup.

FIG. 11 is a diagram indicating the amount of thermo electrons when the end of the filament has a positive potential towards the cup. FIG. 12 is a diagram indicating the amount of thermo electrons when the end of the filament has a negative potential towards the cup. As illustrated in FIG. 11, when another contact point of the filament has a positive potential towards the cup 63, it is difficult for thermo electrons to occur. As illustrated in FIG. 12, when another contact point of the filament has a negative potential towards the cup 63, thermo electrons are prone to occur.

Figure 13:
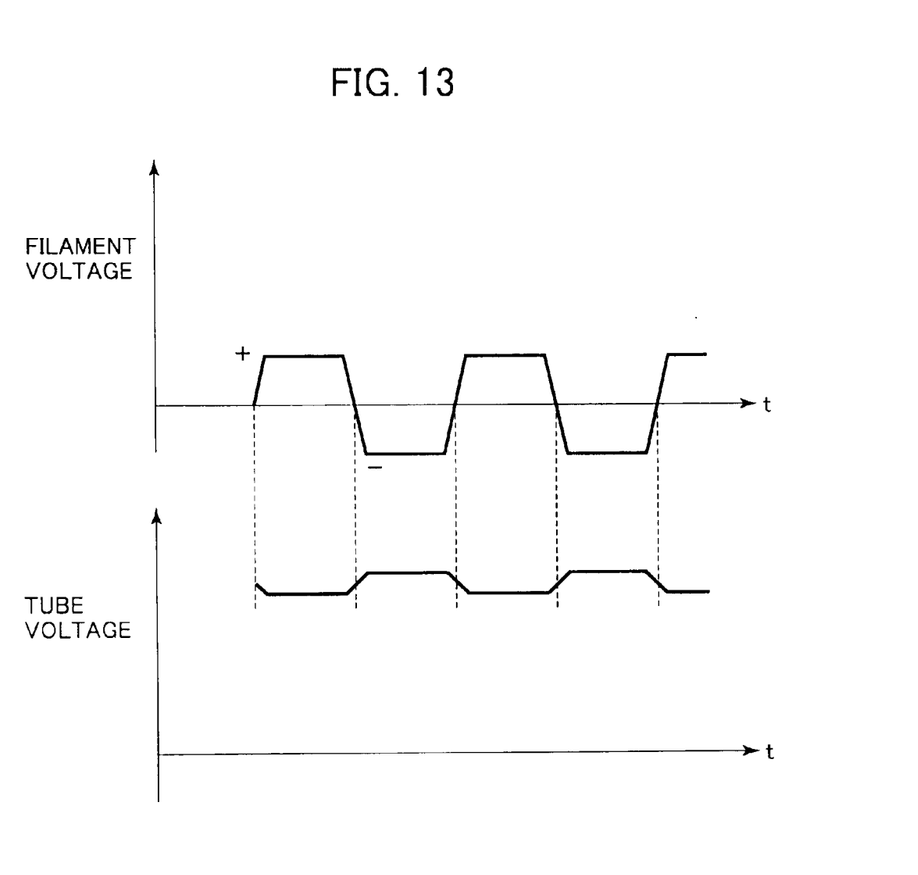
FIG. 13 is a graph of the filament voltage and the tube current.

FIG. 13 is a graph of the filament voltage and the tube current. As illustrated in FIG. 13, when the filament voltage is positive, it is difficult for thermo electrons to occur, causing the tube current to decrease. When the filament voltage is negative, thermo electrons are prone to occur, causing the tube current to increase.

The change in X-ray output is due to one contact point of the cathode 62 connecting to the cup 63, another contact point having potential towards the cup 63, the filament heating frequency fc changing, and thus causing the operation similar to applying a voltage of reverse polarity to the filament voltage to the cup 63 with a function of the grid towards the cathode 62 of the directly heated tube.

Figure 14:
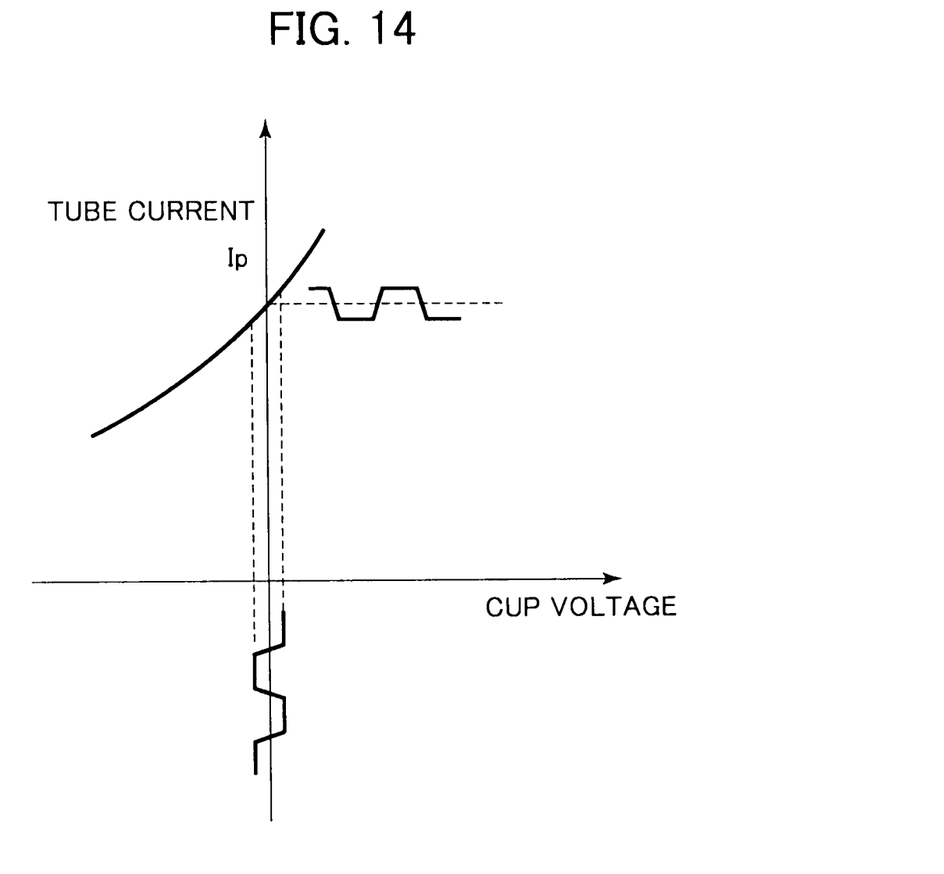
FIG. 14 is a graph illustrating the relationship between the cup voltage and the tube current.

FIG. 14 is a graph illustrating the relationship between the cup voltage and the tube current. As illustrated in FIG. 14, the cup 63 on the cathode 62 side of the X-ray tube 6 functions like the control grid of the triode valve, thus changing the tube current when there is potential towards the filament (cathode of the triode). Then, the cup voltage has reverse polarity to the filament voltage.

In order to prevent the change in X-ray output due to filament heating, there is a method of turning on the filament by a direct current; however, turning on with a direct current causes a problem of declined lifetime due to decreased notching.

Next, the configuration of the third embodiment in order to prevent the fluctuation in X-ray output due to heating of the filament is described with reference to FIG. 15.

The high voltage generator 4a is provided with a filament voltage generator 25a that operates the filament power supply 65. A method is used in which the operating frequency fg of the inverter of the filament voltage generator 25a is made adjustable in correspondence with the revolution cycle T of the X-ray tube 6 and the collection rate R. Furthermore, the filament voltage generator 25a may be referred to as a filament inverter.

Next, the operation of the filament voltage generator 25a is described.

In order to prevent the change in X-ray output due to heating of the filament, there is a method of turning on the filament with a direct current; however, by turning on with a direct current, there is a problem of declined lifetime due to decreased notching. This embodiment is intended to inhibit the effect of changed X-ray output by turning on with alternating current.

Fundamentally, just like the operation of the main inverter 4, the operation of the filament inverter is made adjustable in correspondence with the revolution cycle T [sec] of the X-ray tube 6 and the collection rate R [view/rot].

Regarding correspondence with the fluctuations of the revolution of the X-ray tube 6 (revolution irregularities), it is the same as the inverter operating frequency fi in that the adjustable multiplier (PLL) is used to track the filament inverter.

An example of T=0.35, R=900, the inverter operating frequency fi=24.43 [kHz] (19 times more than the tube voltage switching frequency fs) and the operating frequency fg=24.43 [kHz] of the filament inverter (19 times more than the tube voltage switching frequency fs) is set forth with reference to FIG. 15. FIG. 15 is a time chart illustrating the operating cycle, the tube voltage, and the tube current of the inverter and data collection.

Figure 15:
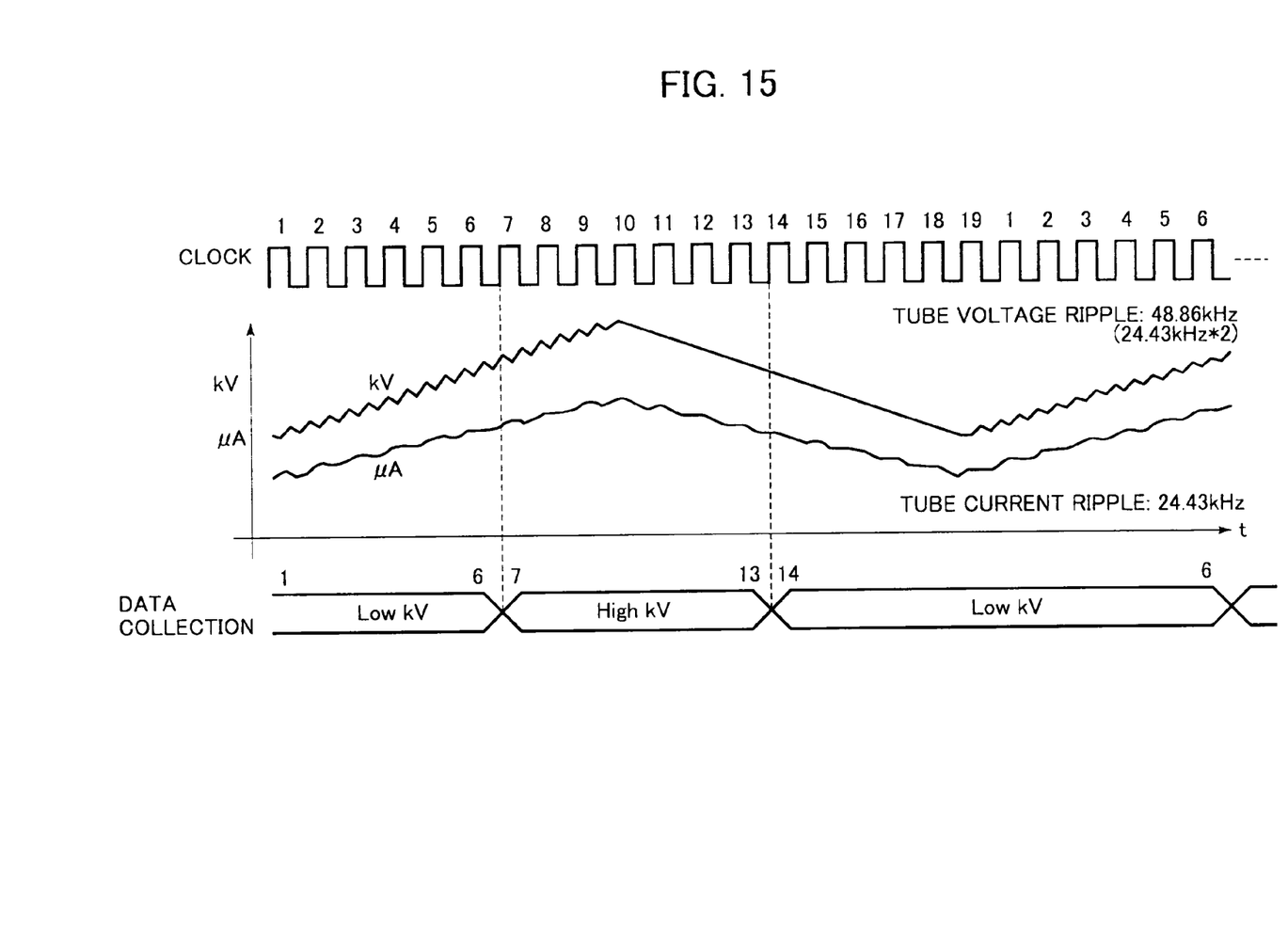
FIG. 15 is a time chart illustrating the operating cycle, the tube voltage, and the tube current of the inverter and data collection.

As illustrated in FIG. 15, at clock 1, the main inverter 4 turns on by receiving up-down instructions and the main inverter 4 increases the tube voltage (Clocks 1 to 9). At clock 10, the main inverter 4 turns off by receiving the up-down instructions and the tube voltage is decreased (clocks 10 to 19). The period from clocks 7 to 13 is determined as the X-ray collecting period under high voltage (High kV), while the period from clocks 1 to 6 and clocks 14 to 19 are determined as the X-ray collecting period under low voltage (Low kV).

There is a ripple in the tube voltage when increasing (clocks 1 to 9). However, when declining (clocks 10 to 19), there are no ripples. Meanwhile, the tube current has a ripple both when increasing and declining. The frequency of a tube voltage ripple is 48.86 (=24.43×2) [kHz]. The frequency of a tube current ripple is 24.43 [kHz].

Therefore, in order to eliminate the effect of the change in X-ray output due to the ripple of the tube current, the filament inverter is operated at a frequency of 24.43 [kHz].

Furthermore, in the embodiment, the fundamental frequency fr was input to the multiplying factor determiner 29, but the multiplier 20 may generate the fundamental frequency fr, for example.

Moreover, the inverter operating frequency fi was prepared using PLL1 and PLL2, etc.; however, in correspondence with the type of combinations of the collection rate R and the revolution cycle T per one revolution of the X-ray tube 6, the inverter operating frequency fi to be synchronized may be obtained in advance and, as a result, the oscillator outputting the clock of the inverter operating frequency fi thereof may be used by switching in correspondence with the collection rate R and the revolution cycle T.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. An X-ray CT system comprising an X-ray tube and an X-ray detector to be arranged opposing to each other, irradiating X-rays from the X-ray tube while revolving around a subject, obtaining an X-ray tube image based on the X-rays detected by the X-ray detector after penetrating the subject, the X-ray CT system comprising:
   a frequency conversion circuit configured to synchronize an operating frequency of an inverter to an integral multiple of a tube voltage switching frequency;
   a high voltage generator having an inverter that supplies a voltage to the X-ray tube by switching between a high voltage and a low voltage at the synchronized operating frequency while revolving the X-ray tube;
   a timing generator configured to send an instruction of data collection based on the synchronized operating frequency and a collection rate, which is the number of the X-ray images obtained per one revolution of the X-ray tube; and
   a data collector configured to collect the X-ray image data based on the instruction of data collection.

2. The X-ray CT system according to claim 1, wherein, the timing generator is configured to send the instruction of data collection at a timing of alternating the voltage supplied to the X-ray tube between monotonic increase and monotonic decrease, and the X-ray CT system comprises:
   an image data acquisition part configured to acquire the X-ray image with a cycle including the monotonic increase and the monotonic decrease, which is half of a cycle of adjusting the voltage supplied to the X-ray tube.

3. The X-ray CT system according to claim 1 or 2, wherein, the X-ray CT system comprises an oscillator that oscillates with the operating frequency near the predetermined fundamental frequency and supplies the operating frequency to the inverter, and
   the frequency conversion circuit is configured to synchronize the operating frequency based on the revolution time per one turn of the X-ray tube and the number of the collection rate, and to set the operating frequency of the oscillator to a frequency that is a multiple of the collection rate, which is the frequency near the fundamental frequency.

4. The X-ray CT system according to claim 3, wherein, the frequency conversion circuit has a frequency detector that computes the revolution frequency of the X-ray tube by detecting the revolution of the X-ray tube per predetermined angle, and
   the frequency conversion circuit is configured to multiply the computed revolution frequency based on the collection rate and a revolution cycle of the X-ray tube, to compare the multiplied revolution frequency with the operating frequency, and to control the oscillator to conform the multiplied revolution frequency to the operating frequency.

5. The X-ray CT system according to claim 3, wherein, the frequency conversion circuit is configured to generate a predetermined frequency and, in correspondence with the collection rate and a revolution cycle of the X-ray tube, multiplies the predetermined frequency by a multiplier and converts the multiplied frequency to the operating frequency of the inverter.

6. The X-ray CT system according to claim 1, wherein, the X-ray tube comprises a cathode, an anode and a cup, to which one contact point of the cathode is connected, the cup having a voltage between another contact point of the cathode, and
   the high voltage generator further applies a filament voltage between the cathode and the anode in a heating frequency synchronized with the predetermined operating frequency during the revolution of the X-ray tube.

* * * * *